United States Patent [19]

van Zelderen

[11] Patent Number: Plant 5,735

[45] Date of Patent: May 6, 1986

[54] ALSTROEMERIA NAMED ZELIDO

[75] Inventor: Gerald J. van Zelderen, Aalsmeer, Netherlands

[73] Assignee: J. van Zelderen & Zn., Aalsmeer, Netherlands

[21] Appl. No.: 652,603

[22] Filed: Sep. 19, 1984

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new alstroemeria variety characterized by the distinctive coloration of its large blossoms with their petals having numerous, sharply-defined, longitudinal flecks or streaks of red-purple against a predominately white background, the outer petals also having central areas shaded in lighter red-purple, and by its upright and vigorous growth habit and continuous production of flowers on its umbel arrangement of branches during each of its blooming seasons.

1 Drawing Figure

BACKGROUND OF THE NEW PLANT

This new alstroemeria originated as a seedling and resulted from my crossing of plants (unpatented) selected from individually-identified members of stock maintained at Aalsmeer, Holland for breeding purposes. This particular seedling was selected by me for propagating and testing because of the distinctive coloration of its large blossoms produced on strong, upright, umbel stems. Specifically, the outer petals have a red-purple central area with white peripheral areas, the inner petals have a white background color throughout, and both inner and outer petals have numerous longitudinal flecks or streaks of darker red-purple. The selected plant was propagated by me at Aalsmeer, Holland through several generations by root division to establish that its distinctive characteristics hold true from generation to generation and appear to be firmly fixed. Breeding efforts commenced in 1978 and propagation is currently being carried on at Aalsmeer, Holland by dividing root stocks.

DESCRIPTION OF THE DRAWING

This new variety of alstroemeria plant is illustrated by the accompanying photographic drawing in full color showing a blooming umbel of the plant with buds and flowers in different stages of opening. The color renditions are believed to be as close to the specified colors as is possible to obtain by conventional photographic procedures.

DESCRIPTION OF THE NEW PLANT

The following is a detailed description of my new alstroemeria plant with color designations according to The R.H.S. Colour Chart of The Royal Horticultural Society of London, England. Cross references to the color names appearing in The Horticultural Colour Chart (H.C.C.) of London, England, are also parenthetically indicated.

THE PLANT

Origin: Seedling.

Parentage:

*Seed parent.*—Breeding Stock Plant No. 780301.

*Pollen parent.*—Breeding Stock Plant No. 770222.

Classification: Alstroemeria Hybrid.

Form: An erect bush having a tall, slender, upright stalk with flower-bearing branches in simple umbel arrangement at its top.

Height: About 170 centimeters.

Growth: Upright, strong, and vigorous.

Root stock: Tuberous.

Foliage:

*Quantity.*—Medium.

*Number of leaves.*—About 20 to 30 per stem.

*Size of leaf.*—Varies depending on season.

*Shape of leaf.*—Elliptic.

*Texture.*—Leathery.

*Color.*—Upper sides and undersides are medium green.

THE BUD

Form: Pear-shaped. The six petals are perianth and there is no calyx.

Size: Medium-to-large.

*Diameter.*—About 1.5 to 2 centimeters.

*Length.*—About 4 centimeters.

Length of peduncle: About 2 to 3.5 centimeters.

THE FLOWER

Blooming habit: Continuous in early Spring and Fall.

Flower size: Large.

*Diameter.*—About 6 centimeters.

*Depth.*—About 6 centimeters.

Borne: Singly.

Shape: Generally funnel-like with petal tips curling outwardly.

Petalage:

*Number of petals.*—Six.

*Arrangement.*—Two concentric circles of three.

*Form.*—Broad oval.

*Texture.*—Leathery.

*Appearance.*—Shiny.

*Color.*—Outer petals — Color of central area is light red-purple 68D (Rhodamine Purple) with white peripheral areas and with intense longitudinal flecks or pencil-stripes of deeper red-purple 64C/64D (Magenta Rose) centrally and of lighter red-purple 68D peripherally. The reverse sides of the outer petals have a background color of 73B or 68B (Roseine Purple) with lighter marginal areas and with darker red-purple flecks or pencil stripes of 58A (Indian Lake). Inside petals — A white base color of 155A with numerous, longitudinal, well-defined flecks or pencil-stripes of red-purple 64C/64D (Magenta Rose).

Persistence: The flowers hang and dry.

Main stem or stalk:

*Length.*—About 170 centimeters.

*Color.*—Light green.

*Character.*—Strong and upright.

*Lasting quality of flower.*—On the plant — 15 to 20 days. As a cut flower — 10 to 15 days.

REPRODUCTIVE ORGANS

Stamens:

*Number.*—Six.

*Arrangement.*—One opposite each petal.

*Anthers.*—Size: About one centimeter. Color: Olive green.

Filaments:

*Length.*—About 4 centimeters.

*Color..*—Light violet/blue.

*Pollen.*—Gray/blue color.

Pistils:

*Number.*—One.

*Styles.*—Length: About 0.8 to 1.2 centimeters. Color: Light violet/blue.

Stigma:

*Color.*—Light violet/blue.

Fruit:

*Shape.*—Capsular.

*Color.*—Light brown.

This plant is particularly noted for the distinctive coloration of its flowers, which coloration does not closely resemble that of any other alstroemeria plant previously known to me. The large blossoms of this varietal have outer petals with red-purple central areas and white peripheral areas, and both the inner and outer petals have numerous, sharply-defined longitudinal flecks of deeper red-purple. The cultivar has a vigorous growth habit and, during its blooming seasons, a continuous production of flowers that resist adverse effects of wet or hot weather and notably retain their coloration after full bloom.

I claim:

1. A new and distinctive alstroemeria cultivar, substantially as shown and described, characterized by the distinctive coloration and continuous production of its large blossoms with their petals having numerous longitudinal streaks of red-purple against a predominately white background and with the outer petals also having central areas of a lighter red-purple background.

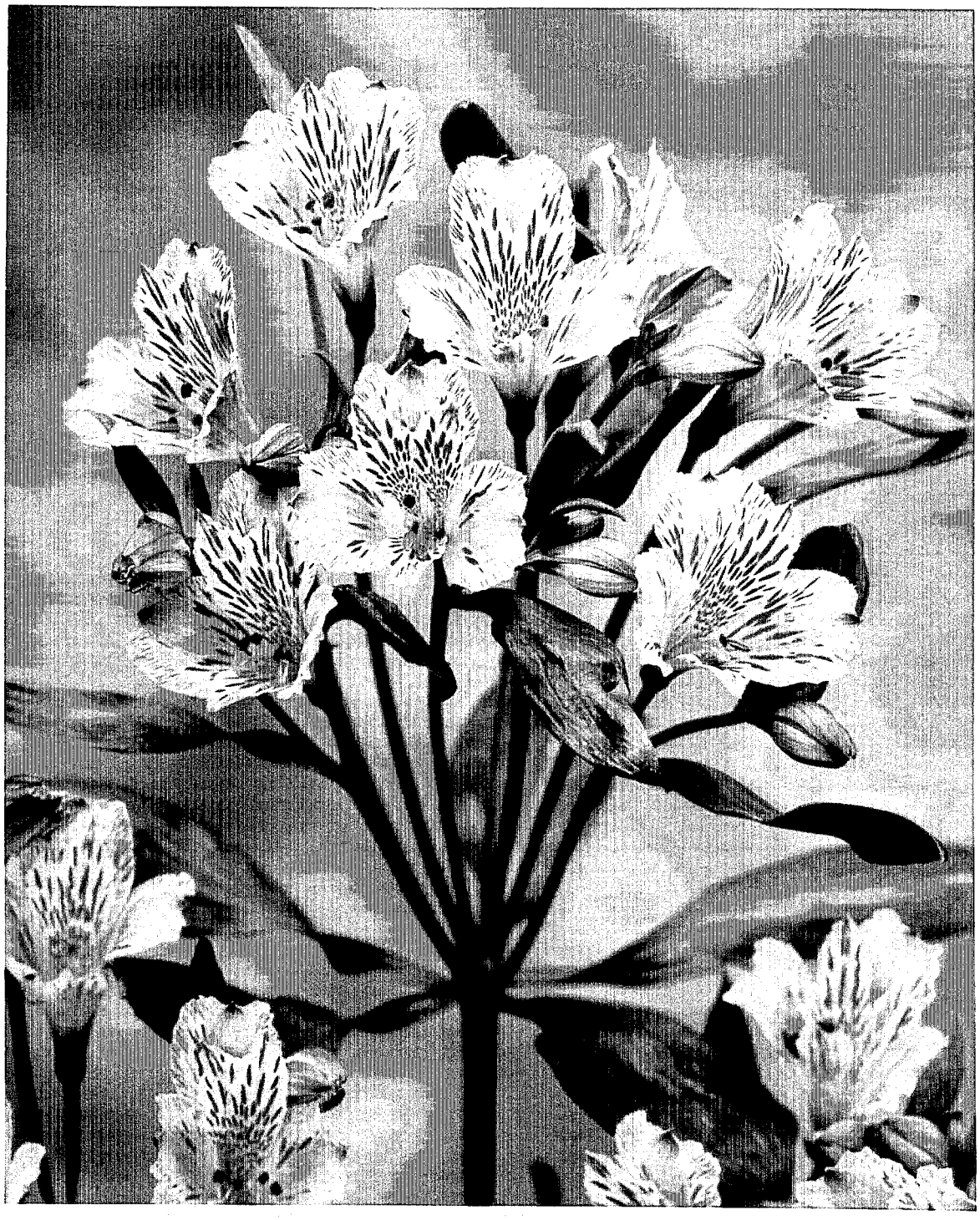

* * * * *